United States Patent [19]

Cho et al.

[11] Patent Number: 4,832,035
[45] Date of Patent: May 23, 1989

[54] TISSUE METABOLISM MEASURING APPARATUS

[75] Inventors: Yoshio Cho, Hyogo; Masahiko Kanda, Osaka, both of Japan

[73] Assignee: Sumitomo Electric Industries, Ltd., Osaka, Japan

[21] Appl. No.: 158,948

[22] Filed: Feb. 22, 1988

[30] Foreign Application Priority Data

Feb. 23, 1987 [JP] Japan .................................. 62-39339
Feb. 17, 1988 [JP] Japan .................................. 63-36203

[51] Int. Cl.$^4$ ............................................. A61B 5/00
[52] U.S. Cl. .................................................. 128/633
[58] Field of Search .............. 128/632, 633, 634, 362; 364/413.07, 413.08, 413.09, 413.1

[56] References Cited

U.S. PATENT DOCUMENTS

| | | | |
|---|---|---|---|
| Re. 31,879 | 5/1985 | Lübbers et al. | 128/633 |
| 4,167,331 | 9/1979 | Nielsen | 128/633 |
| 4,509,522 | 4/1985 | Manuccia et al. | 128/634 |
| 4,704,029 | 11/1987 | Van Heuvelen | 128/633 |
| 4,773,097 | 9/1988 | Suzaki et al. | 364/413.09 |

FOREIGN PATENT DOCUMENTS 2075668 11/1981 United Kingdom .

OTHER PUBLICATIONS

*Soviet Journal of Quantum Electronics*, vol. 8, No. 2; Feb. 1978; pp. 236 to 237, American Institute of Physics, by A. P. Gorchakov et al., an Article Entitled: "Nonlinear Spectrograph Based on a Silver Thiogallate Crystal".

*Optik*, vol. 65, No. 4; Nov., 1983; pp. 327 to 338; published by Wissenschaftliche Verlaggesellschaft, Stuttgart, Federal Republic of Germany, by J. Schneider et al.; an artitle entitled: "Apparatur zur Messung äusserst kleiner Anderungen der optischen Transmission" (Apparatus for Measuring Extremely Small Changes of the Optical Transmission).

"Optical Diffusion in Blood" by C. Johnson in IEEE Transaction on Bio-Medial Engineering, vol. BME-17, No. 2, 1970, pp. 129-133.

*Primary Examiner*—Francis Jaworski
*Assistant Examiner*—George Manuel
*Attorney, Agent, or Firm*—W. G. Fasse; D. H. Kane, Jr.

[57] ABSTRACT

In a tissue metabolism measuring apparatus, light sources (31 to 33) emit rays of different wavelengths; the rays are branched as reference light pulses and sample light pulses through optical fibers (38 and 39); the sample light pulses are transmitted through a living body to be examined; the reference light pulses are delayed by means of mirrors (48 to 50); the sample light pulses transmitted through the living body and the delayed reference light pulses are collected by a lens (44); based on the collected light, a second harmonic of the light is generated by an optical crystal (45); and the second harmonic enters a photomultiplier (72). A photon counter 52 counts photons based on the output of the photomultiplier and calculates an average value of the count output. Further, a delay amount of the reference light pulses is changed and when the delay amount of the reference light pulses with respect to the sample light pulses transmitted through the living body is a predetermined value, the average value of the count output of photons of the second harmonic is determined. Thus, scattered components of the transmitted beam in the living body can be removed based on the average value.

12 Claims, 9 Drawing Sheets

(a) REFERENCE LIGHT PULSE (b) SAMPLE LIGHT PULSE (c) $S(\tau)$

TISSUE METABOLISM MEASURING APPARATUS

BACKGROUND OF THE INVENTION

1. Field of the Invention

The present invention relates to a tissue metabolism measuring apparatus and particularly to a tissue metabolism measuring apparatus for measuring, in a non-invasive manner, changes in an oxygenated state of hemoglobin or a quantity of blood in an organ or other parts of a human body or an animal body as well as changes in an oxidation-reduction action of cytoplasmic cytochrome.

2. Description of the Prior Art

Figure 1:
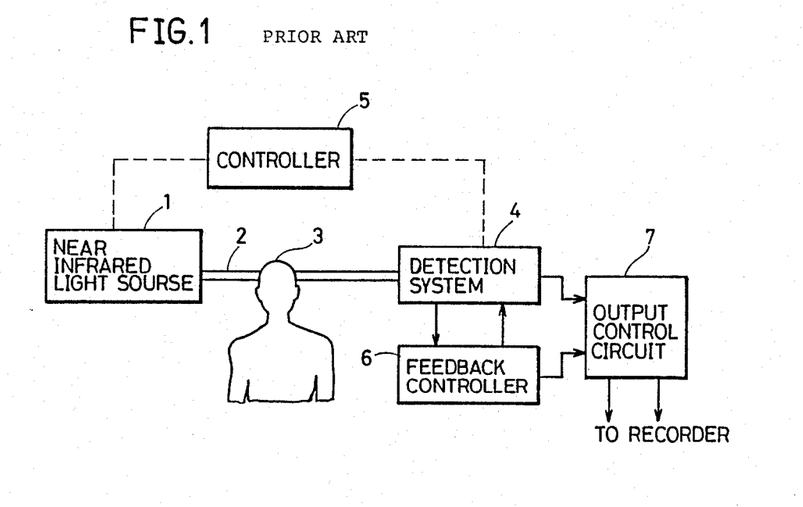
FIG. 1 is a diagram showing a construction of a conventional apparatus for measuring tissue metabolism in a bodily organ.
Figure 2:
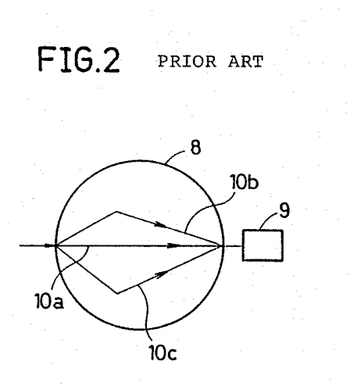
FIGS. 2 and 3 are diagrams showing optical paths of light detected in a conventional apparatus.
Figure 3:
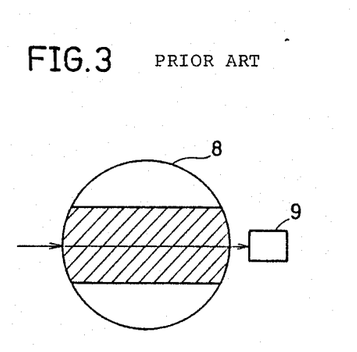

FIG. 1 is a diagram showing a conventional apparatus for measuring a metabolic action in a body organ. FIGS. 2 and 3 are diagrams showing an optical path of light detected in the conventional measuring apparatus.

The apparatus shown in FIG. 1 is described in Japanese Patent Laying-Open Gazette No. 115232/1982. In this apparatus of FIG. 1, a near infrared light source 1 emits alternately near infrared rays of different wavelengths. Each of those near infrared rays passes through the head 3 of a human body by means of an optical fiber 2 so that a detection system 4 measures intensity of the ray. A controller 5 controls transmitting speeds and order of monochromatic flashes and demodulates a detected optical signal. A feedback controller 6 maintains constant the optical signal detected based on one wavelength by negative feedback control of a detection sensitivity and compensates for a change in transmittance caused by a change in a quantity of blood of the organ detected during a fluoroscoping period. An output control circuit 7 outputs a feedback voltage blood quantity indicating signal simultaneously with reception of reference and measuring signals.

The above described apparatus shown in FIG. 1 applies light of a range of 700 nm to 1300 nm to the head 3 and detects light transmitted through the head 3 so as to observe a change in an oxygenated state of hemoglobin or a quantity of blood in the brain as well as a change in an oxidation-reduction action of cytoplasmic cytochrome. This operation is performed by making use of the fact that deoxygenated hemoglobin has a small peak of about 760 nm with an isosbestic point of hemoglobin of 805 nm being used as a reference wavelength or the fact that an absorber dependent on oxygen of cytochrome aa3 exists in a wavelength range of 700 nm to 1300 nm. In addition, Japanese Patent Laying-Open Gazette No. 72542/1985 describes an optical CT apparatus in which a bonded state between oxygen molecules such as hemoglobin or myoglobin in a body and oxygen of protein can be observed quantitatively in a two-dimensional distribution by utilizing light of the wavelength range and absorbing property thereof in the same manner as described above and oxygen density of cytocondria can be observed in a two-dimensional distribution based on an oxidized and reduced state of cytochrome or the like as a constituent of a respiratory chain.

However, if light of the range of 700 nm to 1300 nm has a higher transmittance through a body than that of light in the visible radiation range and if it is applied to the body whereby the transmitted light thereof is detected, the incident light is immediately scattered and absorbed in the body because the wavelength thereof is short compared with the size of hemoglobin, and it follows that the detected light is only a component of diffused light. This is described for example in "Optical Diffusion in Blood" by C. Johnson in IEEE TRANSACTION ON BIO-MEDICAL ENGINEERING Vol. BME-17 No. 2, 1970, pp. 129-133.

More specifically, as shown in FIG. 2, if light irradiated into the body is detected by a detector 9, the light detected by the detector 9 includes not only light passing through an optical path 10a as a straight line connecting the incident point and the detector 9 but also light scattered or diffused and passing through optical paths 10b and 10c rather than the optical path 10a. Thus, when the transmitted light is detected, the path through which the detected light has passed in the body cannot be specified. For example, the apparatus shown in FIG. 1 only makes it possible to obtain information of the whole region subjected to the measurement or an area corresponding to a considerably wider optical path (shown as the hatched portion in FIG. 3) than the optical path 10a as the straight line connecting the incident point and the detector 9, as shown in FIG. 3. Information of such a wide range is useless for a clinical diagnosis of an organic disturbance such as a disturbance of blood circulation in a body or a condition thereof because the location of the disturbance is an important concern.

SUMMARY OF THE INVENTION

Therefore, a primary object of the present invention is to provide a tissue metabolism measuring apparatus capable of measuring tissue metabolism such as a blood circulation condition or a respiration condition at a precisely determined position based on detection of only light of a component straight advancing along a line connecting an incident point of light and a detecting portion.

Briefly stated, the apparatus of the present invention is operated in the following manner. Rays of different wavelengths are emitted from a light source and those rays are branched as a reference beam and a sample beam. Either the reference beam or the sample beam is delayed and the sample beam having passed through a body and the reference beam are collected. A second harmonic is generated based on the collected light. Upon detection of the second harmonic, measurement evaluation means counts photons of the detected second harmonic and the count values are averaged for a predetermined number of counting cycles whereby an average value is obtained. A delay amount of either the sample beam or the reference beam is changed based on the average value. The photon average value is determined and stored for the count value of photons of the second harmonic obtained when the delay amount of the beam with respect to the other non-delayed beam is a predetermined value. The tissue metabolism of the body is evaluated and outputted based on the photon average value of each wavelength.

Therefore, according to the present invention, an average value is obtained for the count value of the photons of the second harmonic measured when the delay amount between the reference beam and the sample beam transmitted through the body is a predetermined value. Consequently, scattered components in the beam transmitted through the body can be removed and only the component straight advancing in the body can be detected. Thus, more accurate position information can be obtained at the time of detecting information of the body by using the transmitted beam.

These objects and other objects, features, aspects and advantages of the present invention will become more apparent from the following detailed description of the present invention when taken in conjunction with the accompanying drawings.

DESCRIPTION OF THE PREFERRED EMBODIMENTS

First, referring to FIGS. 4 to 7, a principle of the present invention will be described. In the respective embodiments of the present invention, ultrashort pulses of high repeat frequency are used. Such ultrashort pulses of high repeat frequency are obtained for example in the following manner. A semiconductor laser is used to generate light pulses having a repeat frequency of 1 GHz and a half duration of several tens of or several p sec (p sec=$10^{-12}$ sec). For example, the ultrashort light pulses shown in FIG. 5 have an interval of $10^{-9}$ sec and $10^9$ pulses per second are generated. Such light pulses can be obtained not only by a semiconductor laser but also by a pigment laser or the like.

Figure 4:
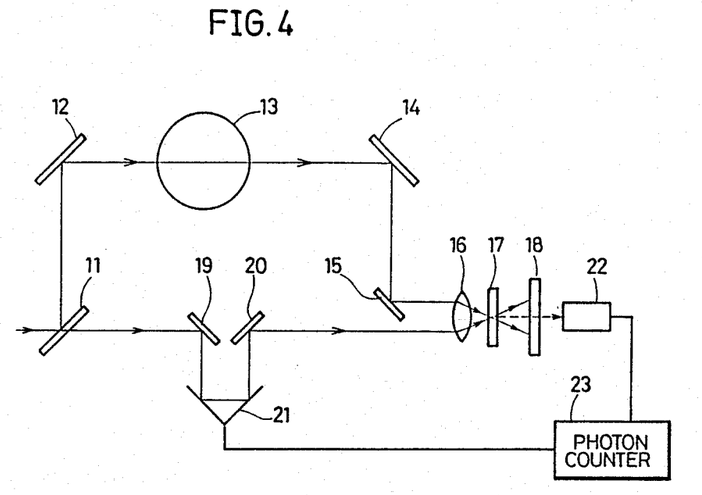
FIG. 4 is a diagram for explaining a principle of the present invention.
Figure 5:
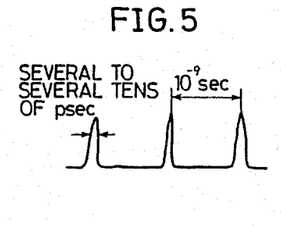
FIG. 5 is a diagram showing an example of an ultrashort light pulse applied to a tissue metabolism measuring apparatus shown in FIG. 4.

The ultrashort light pulses are branched through a half mirror 11 as reference light pulses applied in a straight advancing direction and sample light pulses applied in a direction perpendicular to that of the reference light pulses. The sample light pulses are reflected on a mirror 12 and applied to a body 13 as an object to be measured. The light pulses transmitted through the body are reflected on mirrors 14 and 15 and guided to a lens 16.

On the other hand, the reference light pulses are reflected on a mirror 19 and are guided to a delay path 21. Then, they are reflected on a mirror 20 and enter the lens 16 similarly to the transmitted light pulses. The delay path 21 may be a combination of two mirrors as shown in FIG. 4 or it may be a prism, a corner cube or the like. Operation of the delay path 21 will be described later. The lens 16 collects the transmitted light pulses and the reference light pulses so that they enter a non-linear optical crystal 17.

Figure 6:
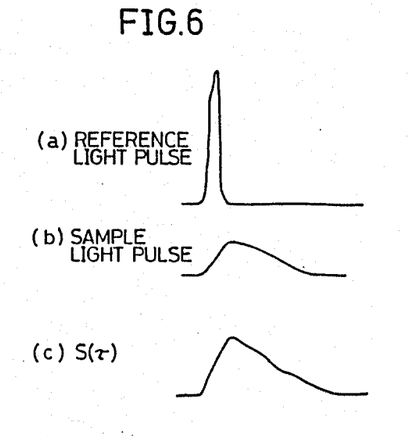
FIG. 6 is a waveform diagram showing a reference light pulse, a light pulse transmitted through a body, and a second harmonic of those pulses.

The reference light pulses and the transmitted light pulses before they enter the non-linear optical crystal 17 have waveforms as shown in FIG. 6. More specifically, the reference light pulses have a slightly reduced power compared with the ultrashort light pulses shown in FIG. 5 but they have the same pulse duration as that of the ultrashort light pulses shown in FIG. 5. On the other hand, the transmitted light pulses have a power extremely reduced by the transmission through the body 13. In addition, as described previously with reference to FIG. 2, beams transmitted through the optical paths 10b and 10c other than the straight advancing path 10a are detected and accordingly the pulse duration of the ultrashort light pulses shown in FIG. 5 cannot be maintained, resulting in a waveform trailing backward. It can be determined however that the rising part of each transmitted pulse represents only the component of the beam transmitted through the straight advancing path 10a shown in FIG. 2. This is because the straight advancing path 10a has the shortest distance among the optical paths in the body 13 and enables the beam therethrough to attain the detector 9 fastest. Thus, application of such pulse having a rapid rise time as the ultrashort light pulses makes it possible to select and detect only the straight advancing component.

The non-linear optical crystal 17 is used to detect only the straight advancing component. The crystal 17 is a crystal of $LiIO_3$, KDP or the like. When the reference light pulses and the transmitted light pulses enter the crystal 17, it generates a second harmonic. Power S of the second harmonic is represented as a function of a delay time $\tau$ corresponding to the distance of the delay path 21 of FIG. 4. Assuming that the reference light pulses are Ir and that the transmitted light pulses are Is, the power S is represented as follows:

$$S(\tau) \sim Is(t) Ir(t-\tau) dt \qquad (1)$$

Consequently, $S(\tau)$ is proportional to a value obtained by integration of a product of $Is(t)$ and $Ir(t-\tau)$. It is of importance that even if the transmitted light pulses are considerably attenuated in the body 13 (according to the results of the real measurement, they are attenuated to $10^{-9}$ of the power of incident light in the head of a rat) and become pulses of very weak light, the output S of the second harmonic, which is the integration value of the product of the transmitted light pulses and the reference light pulses, can be reliably detected because the reference light pulses have a large intensity.

Figure 7:
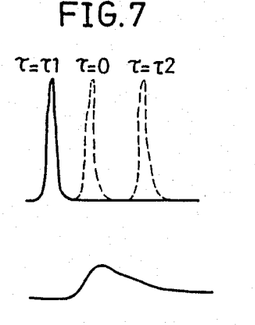
FIG. 7 is waveform diagram for explaining measurement of $S(\tau)$ with respect to delay time of the second harmonic.

The $\tau$ in the above indicated equation (1) represents the delay time corresponding to the distance through the delay path 21 shown in FIG. 4, as described above. More specifically, the delay time is a value obtained by dividing a difference in the distances along the optical paths of the reference light pulses and the transmitted light pulses from the half mirrors 11 to the crystal 17, by light velocity. The value $\tau$ is 0 when the reference light pulses and the transmitted light pulses arrive at the crystal 17 simultaneously as shown in FIG. 7. The reference light pulses are delayed with respect to the sample light pulses as the delay path 21 is changed. In other words, since the output S is the function of the $\tau$, a waveform as shown in (c) of FIG. 6 can be observed if the delay path 21 is changed. In this case, the rising part of the sample light pulse represents the straight advancing component when $\tau=0$. Accordingly, the value of S(0) corresponds to only the straight advancing component and if it is detected, the components of the light scattered through the paths 10b and 10c in the body as shown in FIG. 2 can be removed. Thus, only the component 10a of the straight advancing light can be detected.

The second harmonic outputted from the crystal 17 is emitted in a direction along a medium line of the incident angles of the reference light pulses and the transmitted light pulses as shown by the dotted line in FIG. 4. A wavelength of the second harmonic is ½ of the wavelength of the ultrashort light pulses shown in FIG. 5. The second harmonic is transmitted through a filter 18 and applied to a photomultiplier 22. The filter 18 permits transmission of only a component of the wavelength of the second harmonic. Accordingly, the photomultiplier 22 detects only the component of the second harmonic to output photons.

Figure 8:
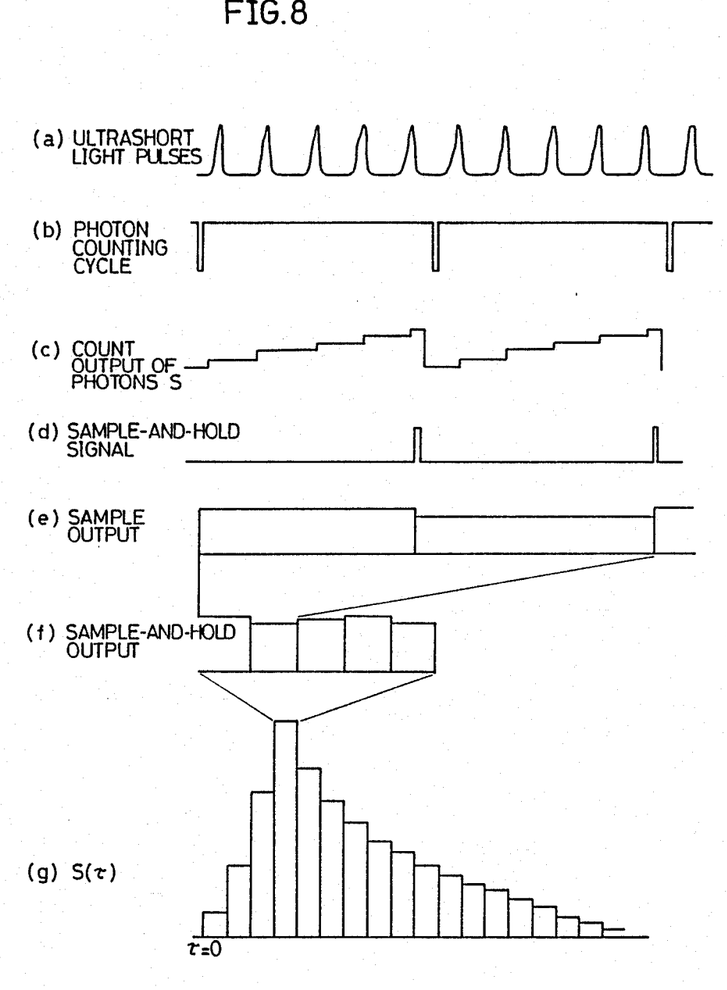
FIG. 8 is waveform diagram for explaining operation for evaluation $S(\tau)$ by a photon counter shown in FIG. 4.

FIG. 8 is a waveform diagram for explaining operation for evaluating the value $S(\tau)$ by a photon counter shown in FIG. 4.

Referring to FIG. 8, operation of the photon counter shown in FIG. 4 will be described. The photon counter 23 is operated as shown in FIG. 8 to obtain a stable output, whereby the value $S(\tau)$ is detected. More specifically, the delay path 21 is provided in a predetermined position and the photon counter 23 counts photons outputted from the photomultiplier 22 at counting cycles as shown in (b) of FIG. 8. In this case, photons are counted for each period in which five ultrashort light pulses pass through the body 13 for example, as shown in (a) of FIG. 8. The number of light pulses to be set for each counting cycle depends on sensitivity for detecting $S(\tau)$. The sensitivity increases with the number of light pulses.

The process of counting of photons is as shown in (c) of FIG. 8. When the count output of photons is sampled by a sample-and-hold signal as shown in (d) of FIG. 8, a sample output as shown in (e) of FIG. 8 is obtained. This output corresponds to the count value of photons for each counting cycle. Those sample outputs are shown in a manner enlarged with respect to the time in (f) of FIG. 8, where an average of five sample outputs for example is evaluated as $S(\tau)$, so that a stable value of $S(\tau)$ is detected. Needless to say, the number of the outputs to be averaged is not limited to five and it is determined dependent on the stability and the sensitivity of the apparatus.

If the delay path 21 of FIG. 4 is changed and the delay time of the reference light pulses is changed to obtain $S(\tau)$, the output as shown in (g) of FIG. 8 is obtained. This value of S(0) is detected as the straight advancing component. Although such processing seems to require much time, the processing speed for evaluating $S(\tau)$ is as fast as described below. Assuming that the light pulses have the conditions of 1 GHz and 10 p sec for example since they are ultrashort light pulses of high repeat frequency, the time required for evaluating $S(\tau)$ with respect to a certain value of $\tau$ is represented in this example by the following equation.

$$10^{-9} \sec \times 5 \times 5 = 2.5 \times 10^{-8} \sec = 25 \text{ n sec}$$

If $S(\tau)$ is obtained with 50 plots, the time required is represented as follows:

$$50 \times 25 \text{ n sec} = 1.25 \text{ } \mu\text{sec}$$

In principle, $S(\tau)$ can be detected with the above indicated speed. However, in practice, a time of about 1 m sec is required because the speed is decreased due to limitations in the photon counting rate of the photomultiplier 22 and the bandwidth of the preamplifier provided adjacent thereto or because a time is required for mechanically setting the delay path 21.

Figure 9:
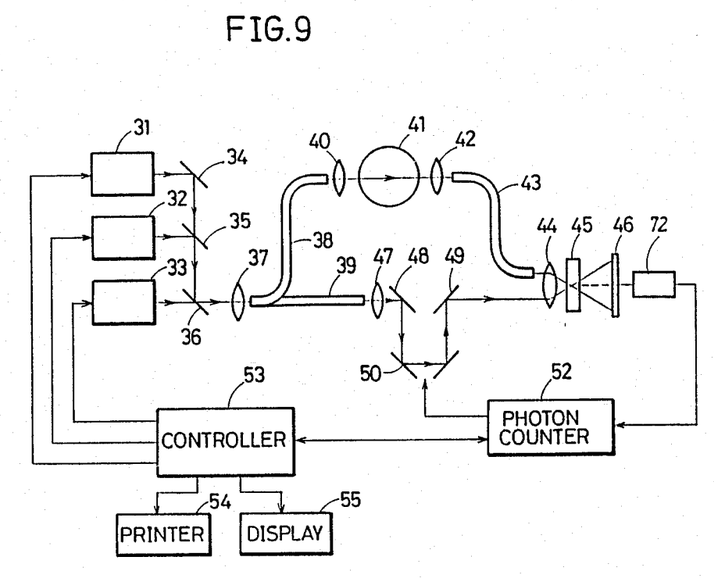
FIG. 9 is a diagram showing a construction of an embodiment of the present invention.
Figure 10:
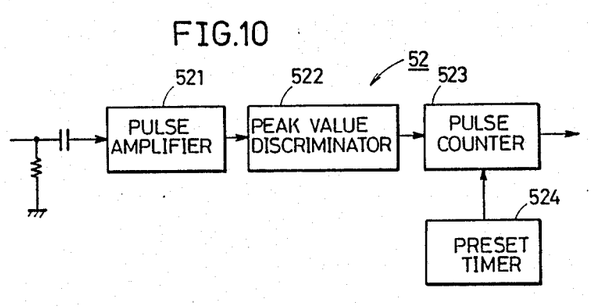
FIG. 10 is a block diagram of a photon counter shown in FIG. 9.
Figure 11:
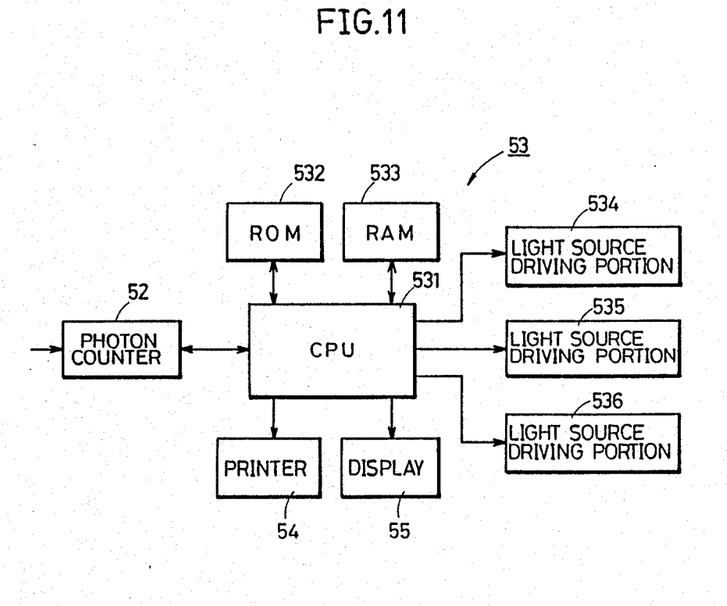
FIG. 11 is a schematic block diagram of a controller shown in FIG. 9.

FIG. 9 is a block diagram showing the entire construction of an embodiment of the present invention. FIG. 10 is concrete block diagram of a photon counter 52 shown in FIG. 9. FIG. 11 is a concrete block diagram of a controller shown in FIG. 9.

Referring to FIGS. 9 to 11, the construction of this embodiment will be described in detail. As shown in FIG. 11, the controller 53 comprises a CPU 531, a ROM 532, a RAM 533 and light source driving portions 534 to 536. The ROM 532 contains a program based on a flow chart shown in FIG. 12 to be described later. The CPU5 31 executes evaluation processing based on the program supplied from the ROM 532, so that data obtained by the evaluation processing is supplied to the RAM 533. The light source driving portions 534 to 536 drive light sources 31 to 33, respectively, shown in FIG. 9. The light sources 31 to 33 generate ultrashort light pulses of high repeat frequency having wavelengths $\lambda 1$, $\lambda 2$ and $\lambda 3$. A pulse duration and a repeat frequency of each wavelength are controlled by the CPU 531 so as to be predetermined values. More specifically, the light sources 31 to 33 each have a shutter and the CPU 531 drive the respective shutters by means of the light source driving portions 534 to 536.

The example shown in FIG. 9 is in principle the same as that of FIG. 4, except that optical fibers 38, 39 and 43 are provided in the example of FIG. 9 in place of the half mirror 11, and the mirrors 12, 14 and 15 in FIG. 4. Ultrashort light pulses generated from the light source 31 enter a lens 37 through a mirror 34 and half mirrors 35 and 36. Ultrashort light pulses generated from the light source 32 enter the lens 37 through the half mirrors 35 and 36. Ultrashort light pulses generated from the light source 33 enters the lens 37 through the half mirror 36.

Ultrashort light pulses of the different wavelengths $\lambda 1$, $\lambda 2$ and $\lambda 3$ having entered the lens 37 are branched as sample light pulses and reference light pulses through the optical fibers 38 and 39, respectively, and the ultrashort light pulses branched through the optical fiber 38 pass through a lens 40 to enter a living body 41. The light pulses transmitted through the body 41 are collected by a lens 44 through a lens 42 and the optical fiber 43 so as to enter a crystal 45.

On the other hand, the reference light pulses branched through the optical fiber 39 are delayed in a delay path 50 through a lens 47 and a mirror 48. Then, they are reflected on a mirror 49 to enter the lens 44. The reference light pulses and the transmitted light pulses collected by the lens 44 enter the crystal 45, by which a second harmonic is generated. The second harmonic thus generated enter a photomultipler 72 through a filter 46. An output of the photomultipler 72 is supplied to a photon counter 52.

The photon counter 52 comprises a pulse amplifier 521, a peak value discriminator 552, a pulse counter 523 and a preset timer 524, as shown in FIG. 10. The pulse amplifier 521 amplifies the output of the photomultipler 72 and the peak vaue discriminator 552 discriminates a peak value of the output of the pulse amplifier 521 and supplies the discriminated pulse signal to the pulse counter 523. The pulse counter 523 counts the number of pulse signals of the discriminated peak value in a period set by the preset timer 524. An output of the photon counter 52 is supplied to the controller 53 and it is also used to control a delay time through the delay path 50. The controller 53 evaluates the above described value of S(0) based on the output of the photon counter 52 and evaluates a quantity of hemoglobin in the body 41, an oxygenation degree of hemoglobin and an oxidation-reduction degree of cytochrome $aa_3$. Those values are printed by a printer 54 and displayed by a display device 55.

Figure 12:
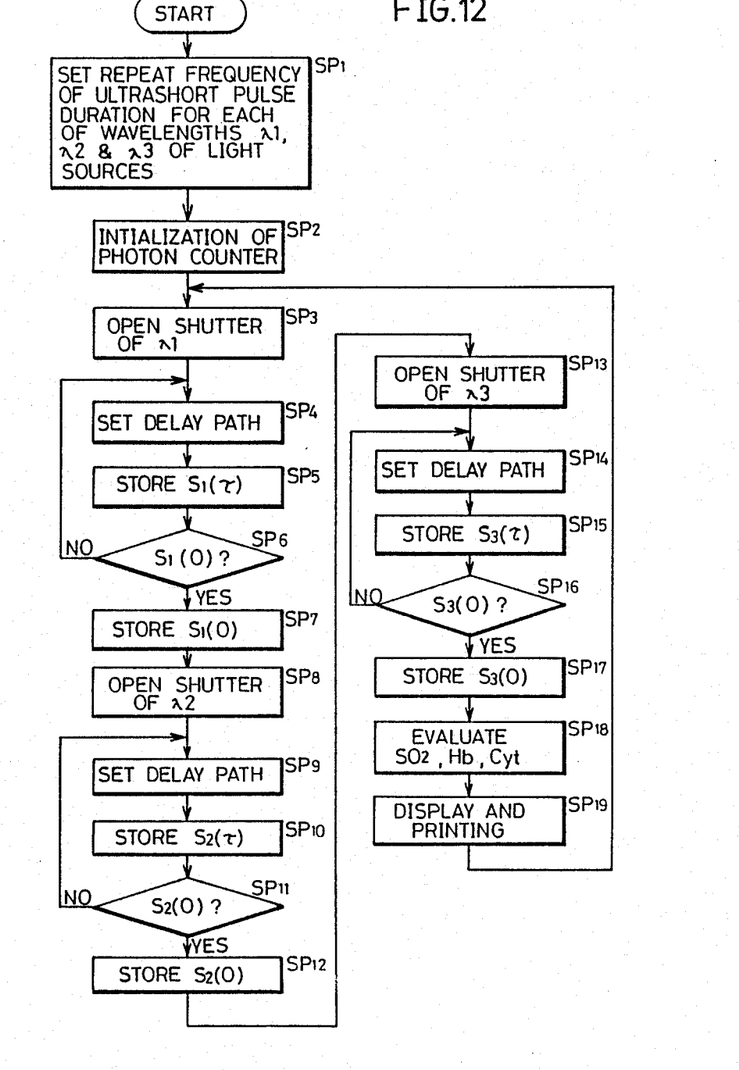
FIG. 12 is a flow chart for explaining operation of the embodiment of FIG. 9.

FIG. 12 is a flow chart for explaining operation of this embodiment.

Referring to FIGS. 9 to 12, concrete operation of this embodiment will be described. In the step SP1, the CPU 531 sets the repeat frequencies of the light pulses having the wavelengths $\lambda 1$, $\lambda 2$ and $\lambda 3$ generated from the light sources 31 to 33 and supplies the set signals to the light source driving portions 534 to 536. Further, the CPU 531 sets an initial preset time of the preset timer 524 for the photon counter 52.

Then, in the step SP3, the CPU 531 opens the shutter included in the light source 31 by the light source driving portion 534 to generate ultrashort light pulses of the wavelength $\lambda 1$. In the step SP4, a delay time through the delay path 50 is set by the photon counter 52. In this step, the photon counter 52 counts photons in a period when the ultrashort light pulses of the wavelength $\lambda 1$ pass through the body 13, and supplies the count output to the CPU 531. The CPU 531 stores $S1(\tau)$ in the RAM 533 in the step SP5 and determines the step SP6 whether $S1(\tau)$ is $S1(0)$ or not. The CPU 531 repeats the operations of the steps SP4 to SP6 until $S1(\tau)$ becomes $S1(0)$. When the CPU 531 determines that $S1(\tau)$ is $S1(0)$, it stores the value $S1(0)$ in the RAM 53 in the step SP7.

Further in the step SP8, the SPU 531 opens the shutter included in the light source 32 by the light source driving portion 535 to generate ultrashort light pulses of the wavelength $\lambda 2$. In the step SP9, the CPU 531 sets a delay time through the delay path 50 by means of the photon counter 52 and in the step SP10, it stores $S2(\tau)$ outputted from the photon counter 52 in the RAM 533. Subsequently in the step SP11, the CPU 531 determines whether $S2(\tau)$ is $S2(0)$ or not. If it is not $S2(0)$, the CPU 531 repeats the operations of the steps SP9 to SP11. When it is determined that $S2(\tau)$ is $S2(0)$, the CPU 531 stores the value $S2(0)$ in the RAM 533 in the step SP12.

In the same manner, the CPU 531 opens the shutter included in the light source 33 by the light source driving portion 536 to generate ultrashort light pulses of the wavelength $\lambda 3$. In the step SP14, the CPU 531 sets a delay time through a delay path 50 by means of the photon counter 52. Then, in the step SP15, the CPU 531 stores $S3(\tau)$ outputted from the photon counter 52 in the RAM 533 in the step SP16, it determines whether the output $S3(\tau)$ is $S3(0)$ or not. If it is not $S3(0)$, the CPU 531 repeats the steps SP14 to SP16. If it is determined that the output is $S3(0)$, the CPU 531 stores the output $S3(0)$ in the RAM 533 in the step SP17. The CPU 531 evaluates the quantity of hemoglobin ($SO_2$) in the body 41, the oxygenation degree (Hb) of hemoglobin and the oxidation-reduction degree of cytochrome $aa_3$ based on the values $S1(0)$, $S2(0)$ and $S3(0)$ stored in the RAM 533. In the step SP19, the results of the evaluation are printed by the printer 54 and displayed on the display device 55.

Figure 13:
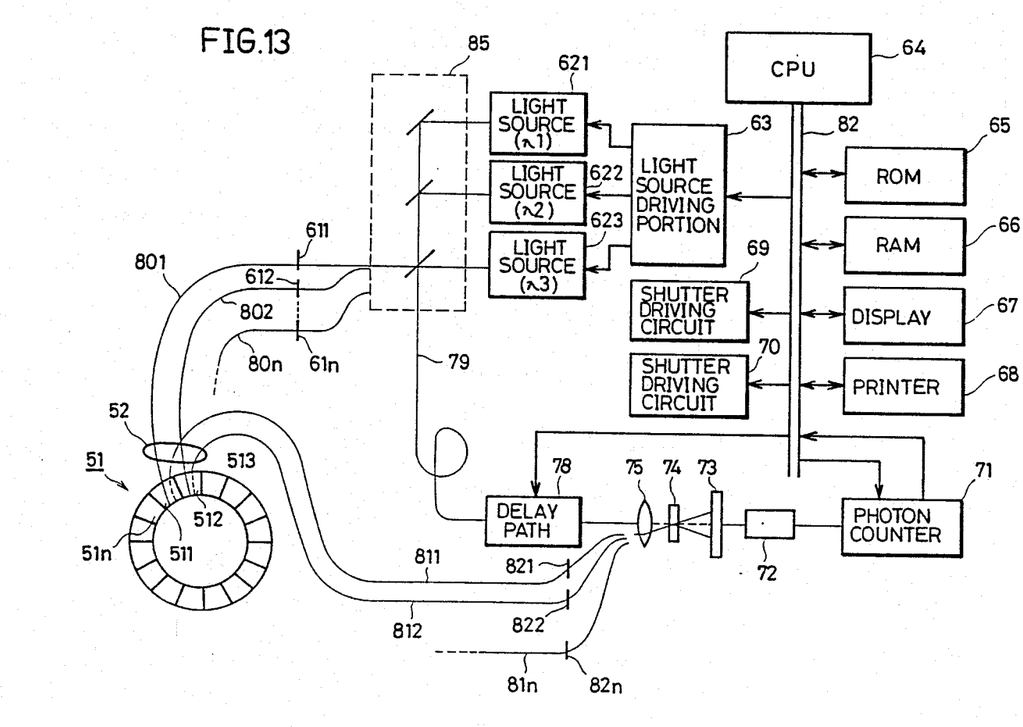
FIG. 13 is a schematic block diagram of another embodiment of the present invention.
Figure 14:
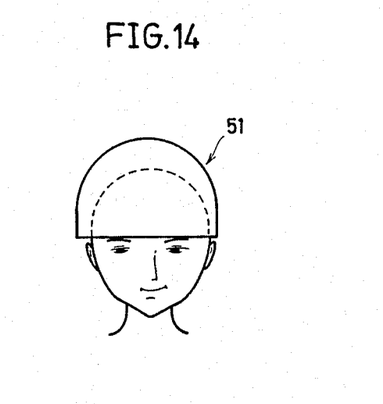
FIG. 14 is an illustration showing a state in which a scanner is attached to the head of a human body.
Figure 15:
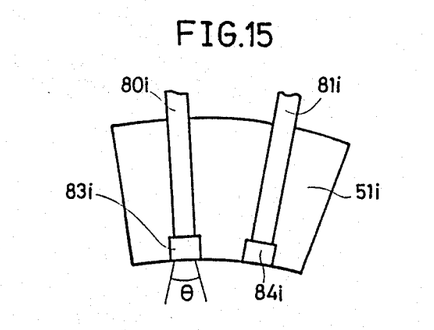
FIG. 15 is a sectional view of a main portion of the scanner.
Figure 16:
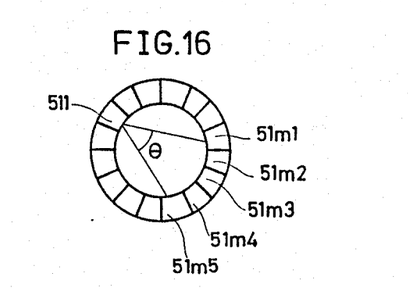
FIG. 16 is a diagram for explaining a sample light pulse transmitted by the scanner.

FIG. 13 is a block diagram showing another embodiment of the present invention. FIG. 14 is a view showing a state in which a scanner portion is put on the head of a person to be examined. FIG. 15 is a sectional view of the scanner portion. FIG. 16 is a diagram showing an irradiation state of light applied from the scanner portion.

Referring to FIGS. 13 to 16, construction of this embodiment will be described. A CPU 64 is connected through a data bus 82 with a ROM 65, a RAM 66, a display device 67, a printer 68, a light source driving portion 63 and shutter driving circuits 69 and 70. The CPU 64, the ROM 65, the RAM 66, the display device 67, the printer 68 and the light source driving portion 63 are identical to those described above in connection with FIG. 4. The light source driving portion 63 is connected with light sources 621 to 623 for generating ultrashort light pulses having wavelengths $\lambda 1$ to $\lambda 3$, respectively. The ultrashort light pulses generated by the light sources 621 to 623 are supplied to an optical branching portion 85.

The optical branching portion 85 is connected with an optical fiber as a reference light path 79 and is also connected with optical fibers as sample light transmitting paths 801 to 80$n$ for guiding different sample light pulses. Shutters 611 to 61$n$ are provided at intermediate points of those sample light paths 801 and 80$n$. When any of those shutters 611 to 61$n$ is opened, sample light pulses are guided in the sample light path corresponding thereto. Ends of the sample light transmitting paths 801 to 80$n$ are connected to the scanner portion 51.

The scanner portion 51 forms a receiver and can be put for example on the head of a person subjected to the measurement as shown in FIG. 14. It is ring-shaped in section and it includes n cells 511 to 51$n$ provided at predetermined intervals on its inner surface. The cells 511 to 51$n$ is connected with the ends of the sample light transmitting paths 80$i$ (i=1 and n) and a top end of each cell is provided with a collecting lens 83$i$. The sample light pulses are collected by the collecting lens 83$i$ so as to be applied with a predetermined angle $\theta$ to an organ of the head of the examined person.

Ends of sample light receiving paths 811 to 81$n$ are provided in the cells 511 to 51$n$, respectively, opposed to the organ. Each end is provided with a collimator lens 84$i$. The sample light pulses transmitted through the body are received by the collimator lens 84$i$ so as to be guided to the collecting lens 75 through the corresponding one of the sample light receiving paths 811 to 81$n$. Shutters 821 to 82$n$ are provided at intermediate points of the sample light receiving paths 811 to 81$n$.

The reference light pulses branched by the branching portion 85 are guided to the collecting lens 75 through the delay path 78 from the reference light path 79. The collecting lens 75 collects the reference light pulses and the sample light pulses so that those collected pulses enter a non-linear optical crystal 74. The non-linear optical crystal 74 generates a second harmonic according to the sample light pulses and the reference light pulses, and the second harmonic is supplied to a photomultiplier 72 through a filter 73. An output of the photomultiplier 72 is supplied to a photon counter 71. The photon counter 71 is the same as the photon counter 52 shown in FIG. 10.

The shutters 611 to 61n provided in the sample light transmitting paths 801 to 80n are driven by the shutter driving circuit 69, while the shutters 821 to 82n provided in the sample beam receiving paths 811 to 81n are driven by the shutter driving circuit 70.

Figure 17:
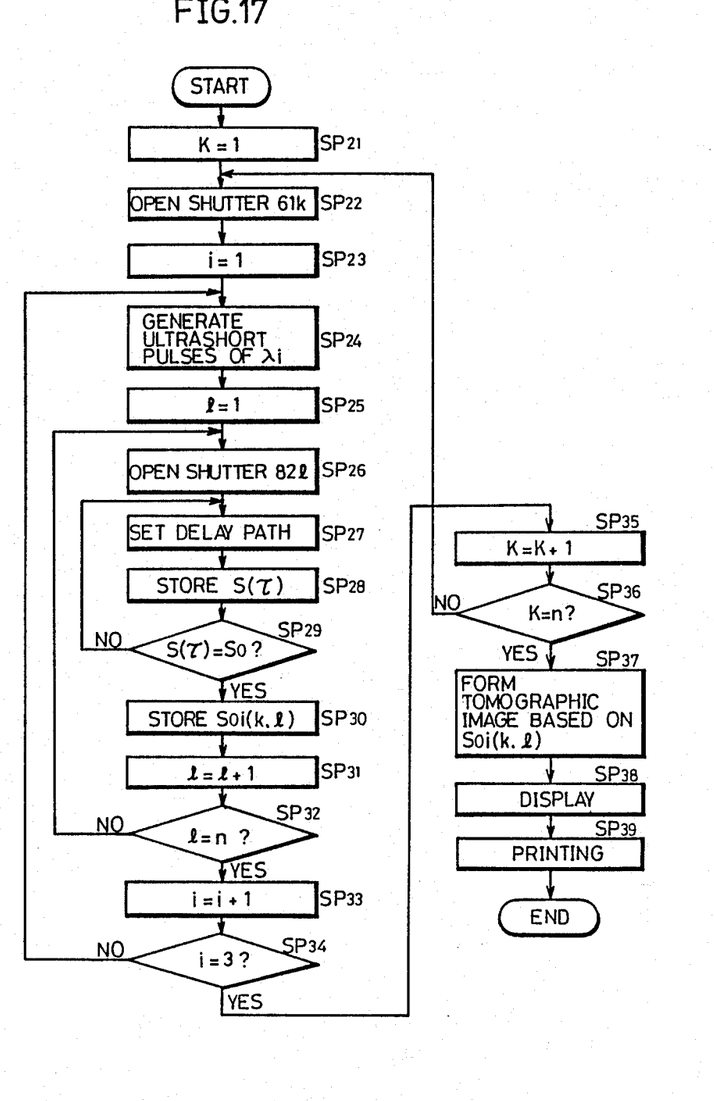
FIG. 17 is a flow chart for explaining concrete operation of the embodiment of FIG. 13.

FIG. 17 is a flow chart for explaining concrete operation of this second embodiment.

Referring to FIGS. 14 to 17, the operation of this embodiment will be described in detail. First, the CPU 64 sets a constant k to 1 in the step SP21. This constant k is used to designate any of the shutters 611 to 61n provided in the sample light transmitting paths 801 to 80n. When the CPU 64 sets the constant k=1, the shutter driving circuit 69 opens the shutter 611 in the step SP22.

Then, the step SP23, the CPU 64 sets a constant i to 1. This constant i is used to designate generation of the ultrashort light pulses of the wavelength $\lambda 1$. When the CPU 64 sets the constant i=1, the light source driving portion 63 generates the ultrashort light pulses of the wavelength $\lambda 1$ from the light source 621 in the step SP24. Thus, the ultrashort light pulses of the wavelength $\lambda 1$ generated from the light source 621 are branched to the sample light transmitting path 801 and the sample light path 79 through the optical branching portion 85, so as to be supplied to the scanner portion 51 through the shutter 611.

The sample light is irradiated from the cell 511 of the scanner portion 51 to the organ with a predetermined opening angle $\theta$ as shown in FIG. 16. The sample light pulses transmitted through the organ are received for example by a cell 51m1.

On the other hand, in the step SP25, the CPU 64 set a constant l to 1. This constant l is used to designate opening of any of the shutters 821 to 82n provided in the sample light receiving paths 811 to 81n. When the constant l=1 is set by the CPU 64, the shutter driving circuit 70 opens the designated shutter in the step SP26. As a result, the sample light pulses received by the cell 51m1 for example in the scanner portion 51 are guided to the lens 75 through the corresponding sample light receiving path.

In the meantime, the CPU 64 sets a delay time of the reference light pulses through the delay path 78 in the step SP27. More specifically, the CPU 64 sets the delay time so that a time required for the sample light pulses to attain the lens 75 through the sample light transmitting path, the organ and the sample light receiving path is equal to a time required for the reference light pulses to attain the lens 75 through the reference light path 79.

The reference light pulses and the sample light pulses are collected by the lens 75 so as to enter the optical crystal 74. Then, the second harmonic is generated by the optical crystal 74 and the second harmonic enters the photomultiplier 72 through the filter 73. The photon counter 71 counts photons based on an output of the photomultiplier 72 and the count output is supplied to the CPU 64. The CPU 64 evaluates $S(\tau)$ based on the output of the photon counter 71 in the step SP28 in the same manner as described above, so that the result of the evaluation is stored in the RAM 66. Further, the CPU 64 determines in the step SP29 whether $S(\tau)$ is $S_0$ or not. If it is not $S_0$, the above described steps SP27 to SP29 are repeated.

When it is determined that $S(\tau)$ is $S_0$, the CPU 64 stores the $S_{01}(1, m1)$ in the RAM 66 in the step SP30. Further in the step SP31, the CPU 64 increments the constant l by 1. Thus, a cell 51m2 adjacent to the cell 51m1 of the scanner portion 51 is enabled to receive the sample light pulses. The CPU 64 determines in the step SP32 whether the constant l is n or not. Thus, it is determined whether the respective shutters of the sample light receiving paths 811 to 81n have been successively opened or not. If the constant l is not n, the CPU 64 opens the shutter corresponding to the cell 51m2 of the scanner portion 51 in the step SP26. By repetition of the above described operation, the sample light pulses of the wavelength $\lambda 1$ are irradiated to the organ and the sample light pulses received by the cells of the scanner portion 51 are successively guided to the optical crystal 74, whereby the values $S_{01}(1, m2)$, $S_{01}(1, m3)$ to $S_{01}(1, n)$ are stored by means of the photon counter 71.

Subsequently, the CPU 64 increments the constant i by 1 in the step SP33 to generate ultrashort light pulses of the wavelength $\lambda 2$ and determines the step SP34 whether the contant i is 3 or not. If the constant is not 3, ultrashort light pulses of the wavelength $\lambda 2$ are generated from the light source 622 in the step SP24. Then, in the same manner as described above, the steps SP25 to SP33 are repeated so that $S_{02}(1, m1)$, $S_{02}(1, m2)$ to $S_{02}(1, n)$ are obtained.

The CPU 64 repeats the operations of the steps SP24 to SP34 for the light pulses of the wavelength $\lambda 2$. Then, the SPU 64 further increments the constant i by 1 and repeats the operations of the steps SP24 to SP34 for the light pulses of the wavelength $\lambda 3$. When the CPU 64 determines in the step SP34 that the constant i is 3, the CPU 64 increments the constant k by 1 in the step SP35 to open the shutter 612 provided in the sample light transmitting path 802. The CPU 64 determines in the step SP36 whether the constant k is n or not. Thus, it is determined whether the respective shutters 611 to 61n have been successively opened or not. If the constant k is not n, the CPU 64 repeats the steps SP22 to SP34 and stores the $S_{0i}(k, l)$ (i being 1, 2 or 3, and k and l being any of 1 to n) in the RAM 66 based on the ultrashort light pulses of the wavelength $\lambda 1$ to $\lambda 3$. When it is determined in the step SP36 that the constant k is n, the CPU 64 processes data according to algorithms for evaluating the quantity of hemoglobin in blood, the saturation degree of oxygen, cytochrome $aa_3$ and the like to obtain tomographic images concerning the quantity of hemoglobin, the oxygenation degrees, cytochrome $aa_3$ and the like in the brain. The results are displayed on the display device 67 in the step SP38 and they are printed by the printer 68 in the step SP39.

Although the head of a human body is examined in the above described embodiments, the body to be examined is not limited to the head of a human body. The form of the scanner portion 51 may be changed suitably according to a body part to be examined, whereby oxygenation degrees and other data of the examined body can be appropriately measured.

In addition, parameters of measurement are not limited to the oxygenation and the like in the brain blood. Other parameters may be applied insofar as they are information of tissue metabolism obtained by measurement of absorption degrees of light.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A tissue metabolism measuring apparatus for measuring tissue metabolism of a living body to be examined by transmitting light in said body, comprising light source means (31, 32, 33) for emitting rays of a plurality of different wavelengths, optical path means (37, 38, 39, 40, 41, 43) for branching the rays emitted from said light source means to a reference beam and a sample beam and guiding said sample beam to said body, delay means (48, 49, 50) provided in said optical path means for delaying either said reference beam or said sample beam, collecting means for collecting said reference beam and said sample beam transmitted through said body, second harmonic generating means (45) for generating a second harmonic light ray based on the beams collected by said collecting means, second harmonic detecting means for detecting the second harmonic light ray generated by said second harmonic generating means, measurement evaluation means (52) for counting photons outputted from said second harmonic detecting means and providing count value outputs for a plurality of count cycles for evaluating an average value by averaging said count values for a prededetermined number of said counting cycles, changing a delay amount of either said sample beam or said reference beam caused by said delay means based on said average value, and for outputting, based on a delay time corresponding to said delay amount and said average value of photons during said delay time, a photon average value obtained by averaging count values of photons of said second harmonic light ray when the delay amount of said sample beam with respect to the reference beam transmitted through said body is a predetermined value, and control means (53) for controlling said light source means and said measurement evaluation means to store said photon average values for the respective wavelengths of said light source means and for outputting a signal indicative of the tissue metabolism in said body based on the photon average values for the respective wavelengths.

2. A tissue metabolism measuring apparatus in accordance with claim 1, wherein
said optical path means include
optical branching means (38, 39) for branching the rays emitted from said light source means to the reference beam and the sample beam,
a reference optical path means (39) for guiding the reference beam branched by said optical branching means to said collecting means, and
a sample optical path means (43) for guiding the sample beam branched by said optical branching means to said body and guiding the sample beam transmitted through said body to said collecting means.

3. A tissue metabolism measuring apparatus in accordance with claim 2, further comprising a receiver means (51) formed in a shape of a ring adapted to surround said living body and including a plurality of cells provided at predetermined intervals along an inner surface thereof, wherein said sample optical path means includes a plurality of sample beam transmitting path means (801 to 80n) having respective ends in the cells of said receiver means (51) being adapted to receive light from said living body, the sample beam branched by said optical branching means being applied to the respective other ends of said path means, and a plurality of sample beam receiving path means (811 to 81n) for guiding the sample beam transmitted through said living body and received by respective ends of said path means to said collecting means.

4. A tissue metabolism measuring apparatus in accordance with claim 3, further comprising
a plurality of first shielding means (611 to 61n) provided corresponding to said plurality of sample beam transmitting path means, respectively, for shielding the sample beams supplied from said optical branching means, wherein
said control means includes first shield driving means (69) for opening any of said first shielding means.

5. A tissue metabolism measuring apparatus in accordance with claim 3, further comprising
a plurality of second shield means (821 to 82n) provided corresponding to said plurality of sample beam receiving path means, respectively, for shielding the sample beam transmitted through said living body, wherein
said control means includes second shield driving means (70) for opening any of said second shield means.

6. A tissue metabolism measuring apparatus in accordance with claim 1, further comprising
filter means (46) provided between said second harmonic generating means and said second harmonic detecting means, for permitting only transmission of said second harmonic light ray.

7. A tissue metabolism measuring apparatus in accordance with claim 6, wherein
said second harmonic generating means includes a non-linear optical crystal (45).

8. A tissue metabolism measuring apparatus in accordance with claim 1, wherein
said control means comprises means for evaluating oxygenation degree of hemoglobin, a quantity of hemoglobin, and oxidation-reduction degrees of cytochrome $aa_3$ as the tissue metabolism occurs in said body.

9. A tissue metabolism measuring apparatus in accordance with claim 8, further comprising display means coupled to said control means (55) for displaying said output signal indicative of the tissue metabolism in said living body, evaluated by said control means.

10. A tissue metabolism measuring apparatus in accordance with claim 8, further comprising
printing means (54) for printing said output signal indicative of the tissue metabolisim in said living body, evaluated by said control means.

11. A tissue metabolism measuring apparatus in accordance with claim 1, wherein said light source means includes a plurality of light sources (31, 32, 33) for emitting the rays of the different wavelengths, and wherein said light source means further comprise means (34, 35, 36) for collecting the rays emitted by said plurality of light sources and guiding the collected rays to said optical paths.

12. A tissue metabolism measuring apparatus in accordance with claim 1, wherein
said control means includes light emission control means (534, 535, 536, 537) for selectively emitting any one of the rays of the different wavelengths from said light source means.

* * * * *